United States Patent
Harris et al.

(10) Patent No.: US 7,604,651 B1
(45) Date of Patent: Oct. 20, 2009

(54) MILITARY CLOTHING HAVING BUILT-IN TOURNIQUETS

(76) Inventors: John Harris, 1200 High Plains Ct., Windsor, CO (US) 80550; Jason Q. Scutt, 5421 Lake Edge Dr., Holly Springs, NC (US) 27540

( * ) Notice: Subject to any disclaimer, the term of this patent is extended or adjusted under 35 U.S.C. 154(b) by 522 days.

(21) Appl. No.: 11/307,269

(22) Filed: Jan. 30, 2006

(51) Int. Cl.
*A61B 17/00* (2006.01)
(52) U.S. Cl. ..................................... 606/203
(58) Field of Classification Search ............... 606/202, 606/203; 2/22, 23, 59, 79, 115, 125, 227, 2/911, 243.1, 69, 114, 247, 250; 128/327
See application file for complete search history.

(56) References Cited

U.S. PATENT DOCUMENTS

| | | | | |
|---|---|---|---|---|
| 2,000,795 | A | * | 5/1935 | Sweeney ..................... 24/432 |
| 2,702,551 | A | * | 2/1955 | Hobson ...................... 606/203 |
| 3,102,311 | A | * | 9/1963 | Martin et al. .............. 24/16 PB |
| 3,747,125 | A | | 7/1973 | Goldman et al. |
| 4,044,759 | A | | 8/1977 | Ghayouran |
| 4,577,622 | A | | 3/1986 | Jennings |
| 4,848,324 | A | | 7/1989 | Gavriely |
| 5,592,953 | A | | 1/1997 | Delao |
| 6,436,064 | B1 | | 8/2002 | Kloecker |
| 6,852,089 | B2 | | 2/2005 | Kloecker et al. |

\* cited by examiner

*Primary Examiner*—Todd E Manahan
*Assistant Examiner*—Jonathan A Hollm
(74) *Attorney, Agent, or Firm*—Ronald E. Smith; Smith & Hopen, P.A.

(57) ABSTRACT

An article of clothing, body armor or garment having at least one limb-receiving sleeve includes a housing secured in encircling relation to the sleeve. A self-sustaining tourniquet is disposed within the housing. An opening is formed in the housing and a cover is provided to close the opening. The tourniquet is positioned fully within the housing when the cover is closed. The tourniquet is oriented in the housing so that a free end of the tourniquet is in registration with the opening. A handle is secured to the free end and is adapted to be grasped by a user when the cover is open. The diameter of the tourniquet is reduced when the handle is pulled upon. A ratchet and pawl structure prevents the tourniquet from loosening after the handle has been pulled.

8 Claims, 3 Drawing Sheets

MILITARY CLOTHING HAVING BUILT-IN TOURNIQUETS

BACKGROUND OF THE INVENTION

1. Field of the Invention

This invention relates, generally, to tourniquets. More particularly, it relates to clothing having tourniquets that are built into both arms and both legs of a military garment.

2. Description of the Prior Art

The widespread use of military and police body armor has reduced body trauma and saved lives. The head and torso of modern military and police personnel are well-protected by helmets and body armor, respectively. Close urban fighting, however, can produce very severe injuries to exposed limbs. To provide protective armor for the legs and arms of such personnel would unduly restrict their freedom of movement, thereby decreasing rather than increasing their chances of survival in a combat zone.

The legs and arms of military or law enforcement personnel are therefore at risk when shots are fired or shells explode. Arterial bleeding from an extremity is now the leading cause of preventable battlefield death in modern warfare. These deaths could be minimized with a rapid and successful tourniquet application.

Modern military organizations are capable of delivering medical services very quickly to wounded personnel. However, in certain military or law enforcement situations, medical services cannot quickly or safely access wounded personnel. Dependent upon the severity of the injury and rate of blood loss, there may be insufficient time to summon and await the services of a tourniquet-supplying medic.

Tourniquets in personal supply kits can be difficult to find and access during trauma and battle confusion. Once the personal supply kit has been located, the injured person may not be able to manipulate or apply the standard tourniquet that comes with such kits over complex fractures and fragmented extremities in a timely and competent fashion.

There is a need, then, to simplify tourniquet application and to shorten the time between the infliction of a wound and the application of a tourniquet so that lives can be saved.

U.S. Pat. No. 4,044,759 to Ghayouran discloses a full leg covering having multiple inflatable air chambers with tourniquets to exert pressure progressively upward from the ankle to the thigh. This structure allows blood in the leg to be slowly "milked" to increase central blood volume during shock or during operative procedures. It requires an air compressor for inflation. The Ghayouran milking device thus shares with the present invention the desirable feature of providing a built-in tourniquet. However, the Ghayouran device differs from the present invention in that it is not self-sustaining, it is not a self-contained, one-piece unit, it lacks a protective pocket cover, and it cannot be applied in one action.

U.S. Pat. No. 2,702,551 to Hobson discloses a garment having a built-in tourniquet at the base of each limb-receiving sleeve. Each built-in tourniquet includes a loop that protrudes from the garment. To use the Hobson tourniquet, the user must 1): locate a separate rigid tool; 2) thread the rigid tool through the loop; 3) twist the tool to tighten the tourniquet; and 4) continue holding the rigid tool until help arrives. The tourniquet will come undone unless the injured party constantly maintains pressure. It is difficult for injured military personnel to maneuver and evade while holding the rigid tool.

When the tourniquet is not in use, the loop, being mounted on the external surface of the garment as aforesaid, can become snagged on various environmental obstacles as the wearer of the garment moves past such obstacles. For example, if the garment is worn in a forest or jungle, underbrush and other natural obstacles may engage the loops. If the garment is worn in a warehouse or other urban setting, various man-made artifacts may engage the loop. The engaging of a loop by an article, whether natural or man-made, that does not quickly release the loop can impede the movement of the garment wearer and thus cause a number of problems.

The Hobson tourniquet thus shares with the present invention the desirable feature of providing a built-in, fast application tourniquet. However, the Hobson device, like the Ghayouran device, differs from the present invention in that it is not self-sustaining, it is not a self-contained, one piece unit, it lacks a protective pocket cover, and it cannot be applied in one action.

Both Ghayouran and Hobson are superior to conventional tourniquets because conventional tourniquets are not built-in with a garment and thus cannot be quickly applied when needed. Conventional tourniquets, Like Ghayouran and Hobson, differ from the present invention in that conventional tourniquets are not self-sustaining, are not self-contained, one piece units, lack a protective pocket cover, and cannot be applied in one action.

The US Army has a tourniquet known by its acronym SAFE tourniquet that is a one-piece, self-contained tourniquet that is self-sustaining. However, it is not built-in to a garment so it cannot be applied as quickly as can a built-in tourniquet. Moreover, it lacks a protective pocket cover and cannot be applied in one action.

Therefore, there is a need for a self-sustaining tourniquet that does not require a user to hold a tool in an operable position while awaiting medical assistance.

There is also a need for a tourniquet-containing garment that includes no external parts that may cause problems for the wearer when the tourniquet is not in use.

A tourniquet that is tightened by twisting a loop is also undesirable because a rigid tool must be available for use and the injured party must be able to thread the loop with such rigid tool if such a tool can be found. The injured party must then rotate the rigid tool a number of times to tighten the tourniquet and then continue to hold the rigid article so that the tourniquet is not loosened until medical assistance arrives.

There is therefore a need for a tourniquet-containing garment that does not require a user to thread a loop or to perform some other such difficult maneuver to tighten a tourniquet.

There is a closely related need for a garment having a built-in tourniquet that does not require a user to find a rigid tool as a condition prerequisite to tightening of the tourniquet.

There is a further need for a tourniquet that does not require the user to hold a tool in an operable position while awaiting medical assistance.

However, in view of the prior art taken as a whole at the time the present invention was made, it was not obvious to those of ordinary skill how the identified needs could be fulfilled.

SUMMARY OF THE INVENTION

The long-standing but heretofore unfulfilled need for a means for a military garment that includes self-sustaining, self-contained, protected tourniquets that are operable by one hand is now met by a new, useful, and non-obvious invention.

An article of clothing having at least one limb-receiving sleeve has a housing mounted in encircling relation to the at least one sleeve. In a practical version of the invention, the article of clothing has four limb-receiving sleeves. Two of the sleeves are adapted to receive the arms of a user and two of the sleeves are adapted to receive the legs of a user. A housing is mounted in encircling relation to each of the limb-receiving sleeves and an opening is formed in each housing. A quickly and easily removable or openable cover is disposed in covering relation to the opening. The cover may incorporate a zipper, a hook and loop fastener, or other suitable releasable fastening means to facilitate quick and easy access to the tourniquet through the opening. An elongate tourniquet is disposed within the housing and is oriented so that an end thereof is in registration with the opening. A handle is secured to the end so that a user can pull the handle and tighten the tourniquet when the cover is open or removed. The tourniquet is wrapped about its associated sleeve so that a second end of the tourniquet underlies the first end so that pulling on the handle reduces the diameter of the tourniquet so that the tourniquet performs its function. The tourniquet assembly preferably includes a ratchet and pawl construction that prevents loosening of the tourniquet after it has been tightened.

The tourniquet is positioned fully within the housing when the cover closes the opening. Accordingly, the tourniquet is self-sustaining, self-contained, and protected when not in use. The tourniquet cannot become snagged or otherwise engaged by an environmental object when not in use. The ratchet and pawl mechanism advantageously prevents unwanted loosening of the tourniquet. Moreover, the one-hand operation for tightening the tourniquet eliminates the need for an injured person to await medical help when a tourniquet is needed.

These and other advantages will become apparent as this disclosure proceeds. The invention includes the features of construction, arrangement of parts, and combination of elements set forth herein, and the scope of the invention is set forth in the claims appended hereto.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
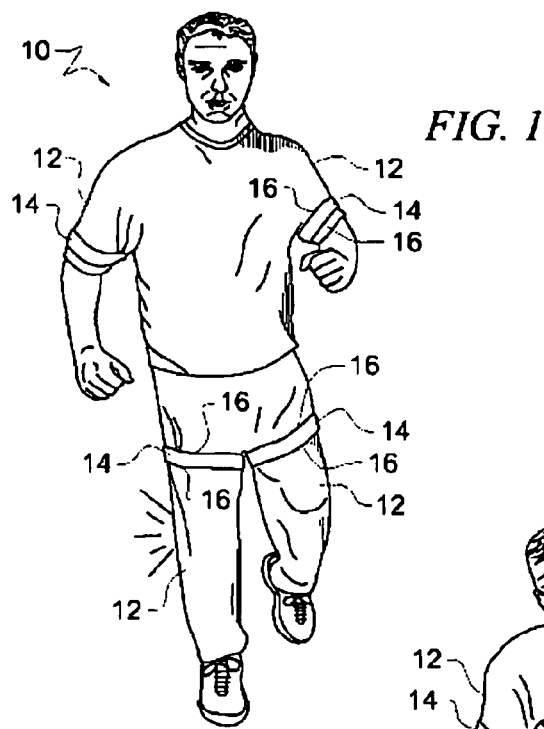
FIG. 1 is a first perspective view of the novel garment.
Figure 2:
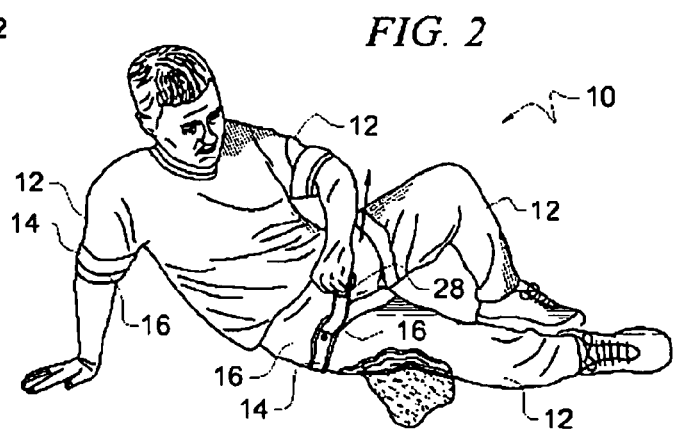
FIG. 2 is a second perspective view thereof.
Figure 3:
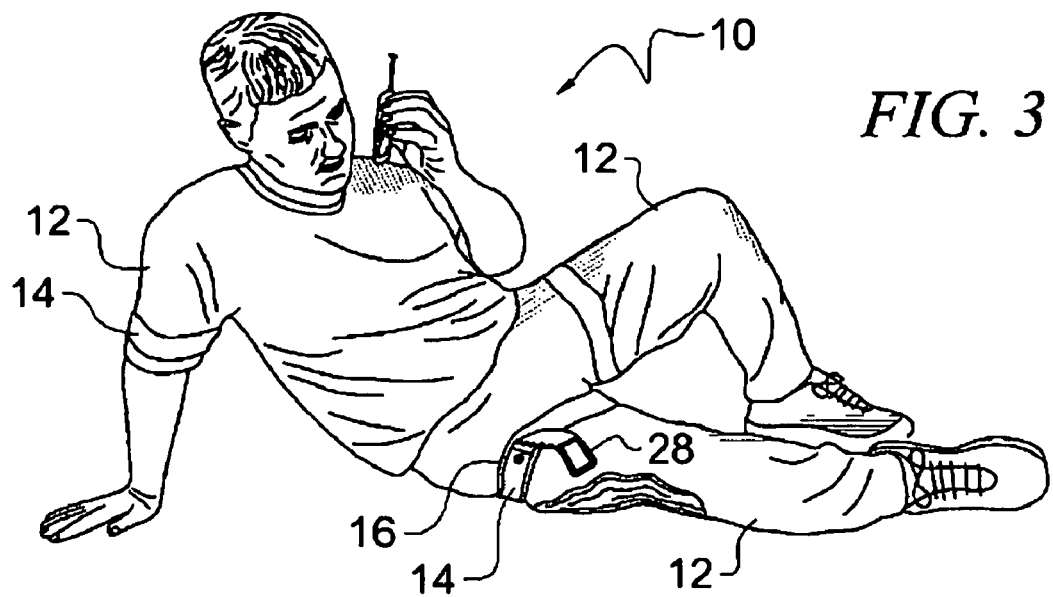
FIG. 3 is a third perspective view thereof.

Referring now to FIGS. 1-3, it will there be seen that an illustrative embodiment of the invention is denoted as a whole by the reference numeral 10. Garment 10 includes two arm-receiving sleeves and two leg-receiving pant legs, collectively denoted 12. Each of these four limb-receiving sleeves or pant legs 12 is provided with the same tourniquet structure.

A person receiving a leg wound in FIG. 1 is depicted tightening the appropriate tourniquet in FIG. 2 and summoning medical assistance in FIG. 3. Significantly, the procedure depicted in FIG. 2 requires only a second or two.

Figure 4:
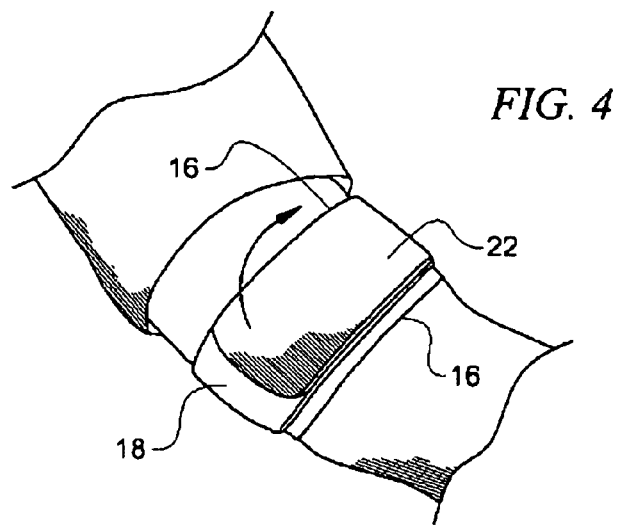
FIG. 4 is a perspective view of a novel tourniquet when its cover is closed.
Figure 5:
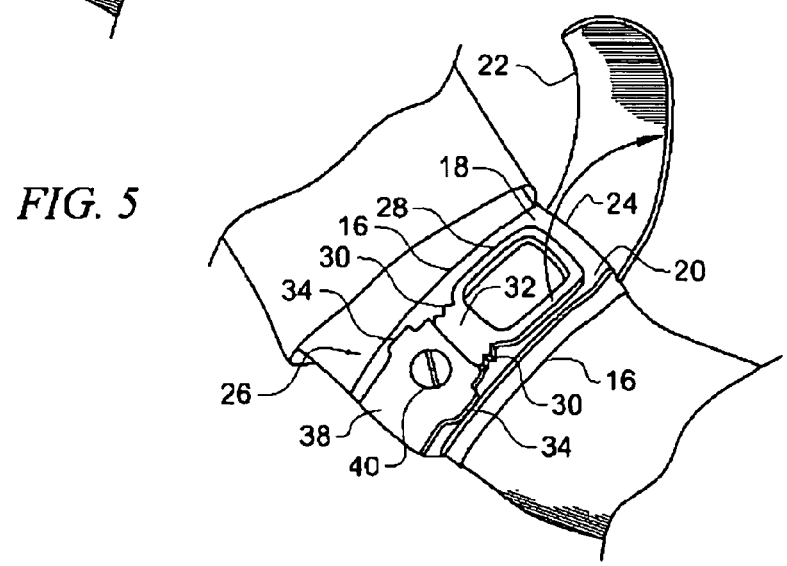
FIG. 5 is a perspective view when the cover is open.
Figure 6:
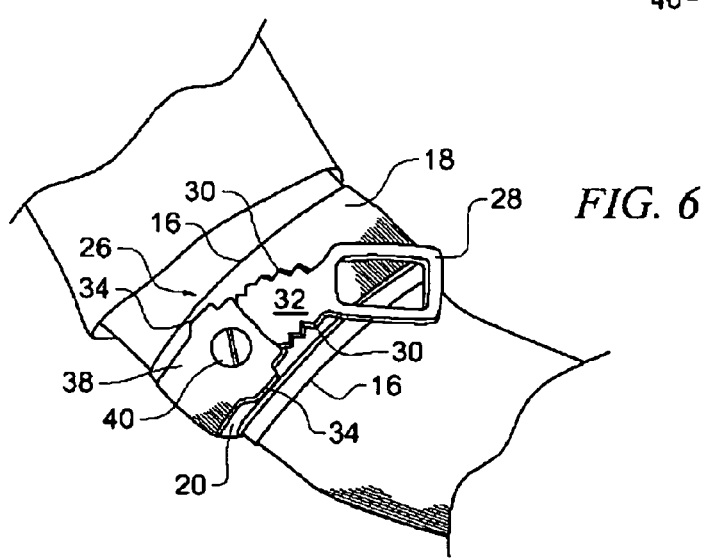
FIG. 6 is a perspective view depicting the tourniquet after the handle thereof has been pulled.

As best understood in connection with FIGS. 4-6, a tourniquet housing 14 may be made by sewing or otherwise permanently affixing a flexible strip of cloth, leather, or other suitable material in overlying relation to an underlying sleeve or pant leg 12 in transverse relation to a longitudinal axis of symmetry of said sleeve or pant leg. Strip 14 is affixed at its peripheral edges 16 only so that an elongate housing is thereby created, within which tourniquet 18 is positioned. The bottom wall of the housing is the pre-existing sleeve or pant leg 12 and the top wall of the housing is the strip of material 14 sewn thereto. The attachment is preferably formed by sewing strip 14 onto a sleeve or pant leg 12 but other suitable attachment means, such as hook and loop fasteners, buttons, strings, snaps and buckles and the like are within the scope of this invention.

In an alternative construction, a housing for a tourniquet has a bottom wall and a top wall that are sewed together or fastened together by other means at their respective peripheral edges so that tourniquet 18 is housed between said top and bottom walls. The housing is then sewed or otherwise attached at its peripheral edges in encircling relation to a limb-receiving sleeve of a garment so that the bottom wall of the housing overlies the preexisting sleeve. Thus, the bottom wall of the housing is not a limb-receiving sleeve 12 as in the first embodiment.

In both constructions, an opening 20 is formed in the top wall of strip 14 to grant access to the tourniquet. In a preferred embodiment, opening 20 has a generally rectangular shape and is opened and closed by a generally rectangular flap or cover 22 that is secured to tourniquet 18 by living hinge 24 (FIG. 5).

A hook and loop fastening material is secured to the top wall of the housing in surrounding relation to opening 20. A complementary hook and loop fastening material is secured to the underside of cover 22 at its periphery so that the mating of said complementary hook and loop materials secures cover 22 in closing relation to opening 20 when tourniquet 18 is not in use, as depicted in FIG. 4. Thus, when no tourniquet is needed, cover 22 is closed and the military personnel wearing the novel garment may travel past various obstacles without running a risk of snagging the garment on such obstacles.

Tourniquet 18 is an elongate, flexible but not longitudinally-stretchable band. A free end thereof is generally denoted 26 in FIGS. 5 and 6. Tourniquet 18 is sufficiently long to wrap completely about an arm or leg. A second end, not depicted, underlies the tourniquet and is held against slipping by the extent of the tourniquet that overlies it.

Handle 28 is secured to the free or first end of tourniquet 18. Handle 28 is adapted to be easily grasped and pulled by one hand as depicted in FIG. 2. Ratchet teeth, collectively denoted 30, are formed in opposite edges of handle neck 32. Pawl teeth, housed in pawl teeth housings collectively denoted 34, are biased into engagement with said ratchet teeth 30 and said ratchet teeth are shaped in a well-known way so that said pawl teeth retract away from ratchet teeth 30 when handle 28 is pulled to tighten tourniquet 18 and so that said pawl teeth engage said ratchet teeth and prevent loosening of the tourniquet when handle 28 is not pulled.

Pawl teeth housings 34 are formed on opposite edges of tourniquet-engaging housing 38 which is hollow and through which handle neck 32 extends. Tourniquet-engaging housing 38, as depicted, is hollow and is secured to the end of housing 18 that is positioned in registration with the opening formed in the housing (first embodiment) or top wall of the housing (second embodiment) so that said tourniquet-engaging housing, like handle 28, is exposed only when cover 22 is open and so that said tourniquet-engaging housing slideably receives the free or first end of the tourniquet therethrough. A quick release button 40, when pressed, causes the pawl teeth to disengage from ratchet teeth 30 so that the tourniquet may be loosened quickly by third party medical personnel or by the injured person if required.

When a tourniquet is needed, it is a simple matter to open cover 22. No tools are required to open the cover, of course. Nor must the injured person learn a new skill to open the cover. Handle 28 of the novel tourniquet will be exposed to view when cover 22 is open, but the injured person need not actually observe the handle. All the injured person has to do is to grab handle 28 and pull it until the bleeding stops. The injured person does not need to find a tool and does not need to thread a tool through a loop.

Instead of cover 22 that is secured in its closed position by hook and loop fasteners, said cover 22 could be permanently sewn into closing relation to opening 20 and a zipper-controlled slot could be formed in said cover. The user would then need to open a zipper to gain access to handle 28. In all other respects, a zipper-accessible tourniquet would share the same structure and operation with the first embodiment.

There are numerous other ways to cover handle 28 so that said handle may be exposed quickly when needed. All of such other ways are within the scope of this invention.

Having stopped the bleeding, the injured person may release his or her grip on handle 28 and await help. The ratchet and pawl or other lockable structure of the tourniquet ensures that it will not slip after having been tightened. If the tourniquet is not provided with quick release button 40, the tourniquet may be made of plastic or other material that may be cut off at an appropriate time after medical help has arrived.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A method for applying a tourniquet, comprising the steps of:
providing an article of clothing including at least one limb-receiving sleeve;
mounting a tourniquet housing having a first end and a second end to said at least one limb-receiving sleeve in encircling relation thereto;
forming an opening in said first end of said tourniquet housing;
providing a releasably attached cover means for covering and uncovering said opening;
positioning a tourniquet having opposite ends in said tourniquet housing;
orienting said tourniquet in said tourniquet housing so that a first end of said opposite ends is in registration with said opening and so that a second end of said opposite ends is disposed in underlying relation to said tourniquet housing;
providing a hollow tourniquet-engaging housing at said first end of said tourniquet housing;
said first end of said tourniquet extending through a hollow interior of said tourniquet-engaging housing;
adapting said first end of said tourniquet to be grasped and pulled by a user when said cover means is open, said pulling reducing a diameter of said tourniquet;
adapting said tourniquet-engaging housing to allow said first end of said tourniquet to slide within said hollow interior of said tourniquet-engaging housing when said first end of said tourniquet is pulled;
adapting said tourniquet-engaging housing to prevent sliding of said tourniquet within said hollow interior of said tourniquet-engaging housing when said first end of said tourniquet is released after having been pulled;
whereby said tourniquet is positioned fully within said tourniquet housing when said cover means is closed; and
whereby said pulling is performed by said user when said cover means is open so that third party medical assistance is not needed to tighten said tourniquet.

2. The method of claim 1, further comprising the steps of:
said step of adapting said first end of the tourniquet to be grasped and pulled by a user including the step of attaching a handle to said first end of said tourniquet;
providing said handle with a handle neck;
forming ratchet teeth on opposite edges of said handle neck;
providing a pawl housing as a part of said tourniquet-engaging housing;
adapting said pawl housing to engage said ratchet teeth to permit tightening of said tourniquet when said handle is pulled upon and adapting said pawl housing to prevent slippage of said tourniquet after said tourniquet has been tightened and said pulling has ended.

3. The method of claim 1, further comprising the steps of;
applying a hook and loop fastener means to an underside of said releasably attached cover; and
applying a mating hook and loop fastener means to said tourniquet housing about a periphery of said opening.

4. The method of claim 1, further comprising the steps of;
covering said opening with a material that is secured to said tourniquet housing about a periphery of said opening;
forming a slot in said material, said slot extending lengthwise in said material; and
providing a zipper for selectively opening and closing said slot so that a user unzips said zipper to gain access to said handle.

5. A method for applying a tourniquet, comprising the steps of:
providing an article of clothing including at least one limb-receiving sleeve;
forming a tourniquet housing by securing together two elongate strips of material at their respective upper and lower edges, said two elongate strips being a top wall and a bottom wall of said tourniquet housing;
mounting said tourniquet housing to said at least one limb-receiving sleeve in encircling relation thereto;
forming an opening in a first end of said top wall of said tourniquet housing;
providing a releasably attached cover means for covering and uncovering said opening;
positioning a tourniquet having opposite ends in said tourniquet housing;
orienting said tourniquet in said tourniquet housing so that a first end of said opposite ends is in registration with said opening and so that a second end of said opposite ends is disposed in underlying relation to said tourniquet housing;
providing a hollow tourniquet-engaging housing at said first end of said tourniquet housing;
said first end of said tourniquet extending through a hollow interior of said tourniquet-engaging housing;

adapting said first end of said tourniquet to be grasped and pulled by a user when said cover means is open, said pulling reducing a diameter of said tourniquet;

adapting said tourniquet-engaging housing to allow said first end of said tourniquet to slide within said hollow interior of said tourniquet-engaging housing when said first end of said tourniquet is pulled;

adapting said tourniquet-engaging housing to prevent sliding of said tourniquet within said hollow interior of said tourniquet-engaging housing when said first end of said tourniquet is released after having been pulled;

whereby said tourniquet is positioned fully within said tourniquet housing when said cover means is closed; and whereby said pulling is performed by said user when said cover means is open so that third party medical assistance is not needed to tighten said tourniquet.

6. The method of claim 5, further comprising the steps of:

said step of adapting said first end of the tourniquet to be grasped and pulled by a user including the step of attaching a handle to said first end of said tourniquet;

providing said handle with a handle neck;

forming ratchet teeth on opposite edges of said handle neck;

providing a pawl housing as a part of said tourniquet-engaging housing;

adapting said pawl housing to engage said ratchet teeth to permit tightening of said tourniquet when said handle is pulled upon and adapting said pawl housing to prevent slippage of said tourniquet after said tourniquet has been tightened and said pulling has ended.

7. The method of claim 5, further comprising the steps of;

applying a hook and loop fastener means to an underside of said releasably attached cover; and applying a mating hook and loop fastener means to said tourniquet housing about a periphery of said opening.

8. The method of claim 7, further comprising the steps of;

covering said opening with a material that is secured to said tourniquet housing about a periphery of said opening;

forming a slot in said material, said slot extending lengthwise in said material; and providing a zipper for selectively opening and closing said slot so that a user unzips said zipper to gain access to said handle.

* * * * *